United States Patent [19]

Rainer

[11] Patent Number: 4,560,693

[45] Date of Patent: Dec. 24, 1985

[54] [1,3]-DIOXOLO[4,5-F]BENZIMIDAZOLES AND [1,4]-DIOXINO[2,3-F]BENZIMIDAZOLES

[75] Inventor: Georg Rainer, Constance, Fed. Rep. of Germany

[73] Assignee: Byk Gulden Lomberg Chemische Fabrik GmbH, Constance, Fed. Rep. of Germany

[21] Appl. No.: 606,873

[22] Filed: May 1, 1984

[30] Foreign Application Priority Data

May 3, 1983 [CH] Switzerland .......................... 2402/83

[51] Int. Cl.⁴ ................ C07D 491/056; A61K 31/435
[52] U.S. Cl. .................................... 514/338; 546/271
[58] Field of Search .................. 546/271; 424/263; 514/338

[56] References Cited

U.S. PATENT DOCUMENTS

| | | | |
|---|---|---|---|
| 4,045,563 | 8/1977 | Berntsson et al. | 424/263 |
| 4,045,564 | 8/1977 | Berntsson et al. | 424/263 |
| 4,182,766 | 1/1980 | Krasso et al. | 546/271 |
| 4,255,431 | 3/1981 | Junggren et al. | 546/271 |
| 4,359,465 | 11/1982 | Ruwart | 424/263 |
| 4,435,406 | 3/1984 | Krasso | 424/263 |
| 4,472,409 | 9/1984 | Senn-Bilfinger | 546/271 |

FOREIGN PATENT DOCUMENTS 2082580  3/1982  United Kingdom .

Primary Examiner—Jane T. Fan
Attorney, Agent, or Firm—Berman Aisenberg & Platt

[57] ABSTRACT

Tricyclic ethers of the general formula I

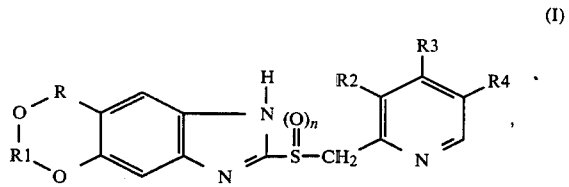

wherein $-R-$ represents a bond and R1 represents a 1-2C-alkylene radical which is completely or partly substituted by fluorine, or a chlorotrifluoroethylene radical, or R and R1 each represent a difluoromethylene radical, R2 represents hydrogen or a 1-3C-alkyl radical, R3 represents hydrogen or a 1-3C-alkyl or 1-3C-alkoxy radical, R4 represents hydrogen or a 1-3C-alkyl radical and n represents the number 0 or 1, and their salts are new compounds with a marked protective effect on the stomach.

22 Claims, No Drawings

[1,3]-DIOXOLO[4,5-F]BENZIMIDAZOLES AND [1,4]-DIOXINO[2,3-F]BENZIMIDAZOLES

FIELD OF THE INVENTION

The invention relates to new tricyclic ethers, processes for their preparation, their use and medicaments containing them. The compounds according to the invention are used in the pharmaceutical industry as intermediates and for the preparation of medicaments.

PRIOR ART

The UK Patent Application GB No. 2 082 580 describes tricyclic imidazole derivatives which are said to inhibit the gastric acid secretion and to prevent the formation of ulcers.

It has now been found, surprisingly, that the tricyclic ethers which are described below in more detail have interesting and unexpected properties which advantageously distinguish them from the known compounds.

DESCRIPTION OF THE INVENTION

The invention relates to new tricyclic ethers of formula I

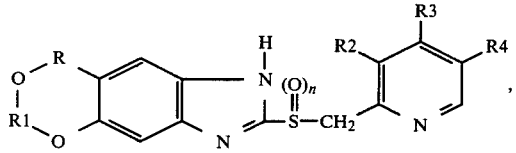

(I)

wherein
  $\frown$R$\frown$ represents a bond and
  R1 represents a 1-2C-alkylene radical which is completely or partly substituted by fluorine, or a chlorotrifluoroethylene radical, or
  each of R and R1 represents a difluoromethylene radical,
  R2 represents hydrogen or a 1-3C-alkyl radical,
  R3 represents hydrogen or a 1-3C-alykl or 1-3C-alkoxy radical,
  R4 represents hydrogen or a 1-3C-alkyl radical and
  n represents the number 0 or 1,
and salts of these compounds.

Examples of 1-2C-alkylene radicals which are completely or partly substituted by fluorine are 1,1-difluoroethylene (—CF$_2$—CH$_2$—), 1,1,2,2-tetrafluoroethylene (—CF$_2$—CF$_2$—) and, in particular, difluoromethylene (—CF$_2$—) and 1,1,2-trifluoroethylene (—CF$_2$—CHF—).

1-3C-Alkyl radicals are propyl, isopropyl, ethyl and, in particular, methyl.

Besides the oxygen atom, 1-3C-alkoxy radicals contain the mentioned 1-3C-alkyl. The methoxy radical is preferred.

Illustrative salts of compounds of formula I in which n denotes the number 0 (sulfides) are above all the acid addition salts. The pharmacologically acceptable salts of the inorganic and organic acids customarily used in galenics are particularly noteworthy. Pharmacologically unacceptable salts, which may initially be obtained, for example, as process products in the preparation of the compounds according to the invention on an industrial scale, are converted into pharmacologically acceptable salts by processes which are known to the expert. Examples of suitable salts are water-soluble and water-insoluble acid addition salts, such as the hydrochloride, hydrobromide, hydroiodide, phosphate, nitrate, sulfate, acetate, citrate, gluconate, benzoate, hibenzate, fendizoate, butyrate, sulfosalicylate, maleate, laurate, malate, fumarate, succinate, oxalate, tartrate, amsonate, embonate, metembonate, stearate, tosilate, 2-hydroxy-3-naphthoate, 3-hydroxy-2-naphthoate and mesilate.

Illustrative salts of compounds of formula I in which n denotes the number 1 (sulfoxides) are above all the basic salts, in particular pharmacologically acceptable salts with inorganic and organic bases customarily used in galenics. Examples of basic salts are the sodium, potassium, calcium or aluminum salts.

Tricyclic ethers of formula Ia

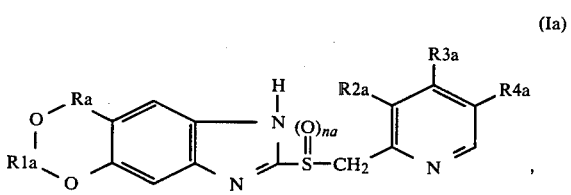

(Ia)

wherein
  $\frown$Ra$\frown$ is a bond,
  R1a is a 1-2C-alkylene radical which is completely or partly substituted by fluorine,
  R2a represents hydrogen or a 1-3C-alkyl radical,
  R3a represents hydrogen or a 1-3C-alkyl or 1-3C-alkoxy radical,
  R4a represents hydrogen or a 1-3C-alkyl radical and
  na represents the number 0 or 1,
and salts of these compounds constitute an embodiment (embodiment a) of the invention.

Illustrative compounds of embodiment a are those of the formula Ia wherein Ra represents a bond, R1a represents difluoromethylene or 1,1,2-trifluoroethylene, R2a represents a hydrogen atom or methyl, R3a represents a hydrogen atom or methoxy, R4a represents a hydrogen atom or methyl and na represents the number 0 or 1, and wherein R2a, R3a and R4a are not simultaneously hydrogen atoms, and salts of these compounds.

Tricyclic ethers of formula Ib

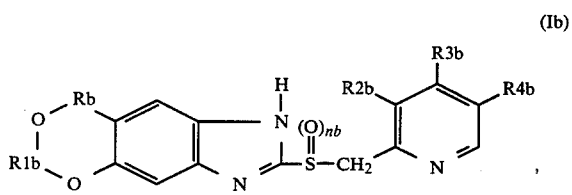

(Ib)

wherein
  $\frown$Rb$\frown$ represents a difluoromethylene radical,
  R1b represents a difluoromethylene radical,
  R2b represents hydrogen or a 1-3C-alkyl radical,
  R3b represents hydrogen or a 1-3C-alkyl or 1-3C-alkoxy radical,
  R4b represents hydrogen or a 1-3C-alkyl radical and
  nb represents the number 0 or 1,
and salts of these compounds, constitute another embodiment (embodiment b) of the invention.

Illustrative compounds of embodiment b are those of formula Ib wherein Rb represents difluoromethylene, R1b represents difluoromethylene, R2b represents a hydrogen atom or methyl, R3b represents a hydrogen atom or methoxy, R4b represents a hydrogen atom or methyl and nb represents the number 0 or 1, and wherein R2b, R3b and R4b are not simultaneously hydrogen atoms, and the salts of these compounds.

Tricyclic ethers of formula Ic

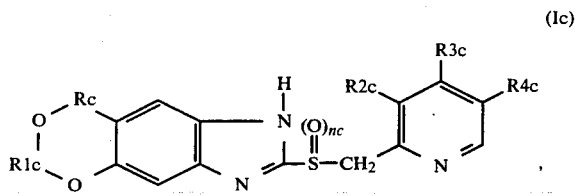

wherein

⁀Rc⁀ is a bond,

R1c is a chlorotrifluoroethylene radical,

R2c represents hydrogen or a 1–3C-alkyl radical,

R3c represents hydrogen or a 1–3C-alkyl or 1–3C-alkoxy radical,

R4c represents hydrogen or a 1–3C-alkyl radical and nc represents the number 0 or 1, and salts of these compounds, constitute a further embodiment (embodiment c) of the invention.

Illustrative compounds of embodiment c are those of formula Ic, wherein Rc represents a bond, R1c represents chlorotrifluoroethylene, R2c represents a hydrogen atom or methyl, R3c represents a hydrogen atom or methoxy, R4c represents a hydrogen atom or methyl and nc represents the number 0 or 1, and wherein R2c, R3c and R4c are not simultaneously hydrogen atoms, and salts of these compounds.

Preferred compounds of the invention are those of the formula I, wherein R represents a bond, R1 represents difluoromethylene, 1,1,2-trifluoroethylene, or 1-chloro-1,2,2-trifluoroethylene, R2 represents hydrogen or methyl, R3 represents methoxy, R4 represents hydrogen or methyl and n represents the number 0 or 1, and pharmacologically acceptable salts of these compounds.

Preferred compounds of the invention are furthermore those of embodiment a, wherein Ra represents a bond, R1a represents difluoromethylene or 1,1,2-trifluoroethylene, R2a represents hydrogen or methyl, R3a represents methoxy, R4a represents hydrogen or methyl and na represents the number 0 or 1, nd pharmacologically acceptable salts of these compounds.

Preferred compounds of the invention are moreover those of embodiment c, wherein Rc represents a bond, R1c represents 1-chloro-1,2,2-trifluoroethylene, R2c represents hydrogen or methyl, R3c represents methoxy, R4c represents hydrogen or methyl and nc represents the number 0 or 1, and pharmacologically acceptable salts of these compounds.

Further examples of compounds according to the invention are:

2,2-difluoro-6-[(3,5-dimethyl-2-pyridyl)methylsulfinyl]-5H-[1,3]-dioxolo-[4,5-f]benzimidazole, 2,2-difluoro-6-[(3,5-dimethyl-2-pyridyl)methylthio]-5H-[1,3]-dioxolo-[4,5-f]benzimidazole, 2,2-difluoro-6-[(4-methyl-2-pyridyl)methylthio]-5H-[1,3]-dioxolo-[4,5-f]benzimidazole, 2,2-difluoro-6-[(4-methyl-2-pyridyl)methylsulfinyl]-5H-[1,3]-dioxolo-[4,5-f]benzimidazole, 6-[(4-ethoxy-2-pyridyl)methylthio]-2,2-difluoro-5H-[1,3]-dioxolo-[4,5-f]-benzimidazole, 6-[(4-ethoxy-2-pyridyl)methylsulfinyl]-2,2-difluoro-5H-[1,3]-dioxolo-[4,5-f]benzimidazole, 6-[(4-ethoxy-3-methyl-2-pyridyl)methylthio]-2,2-difluoro-5H-[1,3]-dioxolo[4,5f]benzimidazole, 6-[(4-ethoxy-3-methyl-2-pyridyl)methylsulfinyl]-2,2-difluoro-5H-[1,3]-dioxolo[4,5-f]benzimidazole, 6,6,7-trifluoro-6,7-dihydro-2-[(3-methyl-2-pyridyl)methylthio]-1H-[1,4]-dioxino[2,3-f]benzimidazole, 6,6,7-trifluoro-6,7-dihydro-2-[(3-methyl-2-pyridyl)methylsulfinyl]-1H-[1,4]-dioxino[2,3-f]benzimidazole, 6,6,7-trifluoro-6,7-dihydro-2-[(3,5-dimethyl-2-pyridyl)methylthio]-1H-[1,4]-dioxino[2,3-f]benzimidazole, 6,6,7-trifluoro-6,7-dihydro-2-[(3,5-dimethyl-2-pyridyl)methylsulfinyl]-1H-[1,4]-dioxino[2,3-f]benzimidazole, 6,6,7-trifluoro-6,7-dihydro-2-[(4-methyl-2-pyridyl)methylthio]-1H-[1,4]-dioxino[2,3-f]benzimidazole, 6,6,7-trifluoro-6,7-dihydro-2-[(4-methyl-2-pyridyl)methylsulfinyl]-1H-[1,4]-dioxino[2,3-f]benzimidazole, 2-[(4-ethoxy-2-pyridyl)methylthio]-6,6,7-trifluoro-6,7-dihydro-1H-[1,4]-dioxino[2,3-f]benzimidazole, 2-[(4-ethoxy-2-pyridyl)methylsulfinyl]-6,6,7-trifluoro-6,7-dihydro-1H-[1,4]-dioxino[2,3-f]benzimidazole, 2-[(4-ethoxy-3-methyl-2-pyridyl)methylthio]-6,6,7-trifluoro-6,7-dihydro-1H-[1,4]-dioxino[2,3-f]benzimidazole, 2-[(4-ethoxy-3-methyl-2-pyridyl)methylsulfinyl]-6,6,7-trifluoro-6,7-dihydro-1H-[1,4]-dioxino[2,3-f]benzimidazole, 6,6-difluoro-6,7-dihydro-2-[(4-methoxy-2-pyridyl)methylthio]-1H-[1,4]-dioxino[2,3-f]benzimidazole, 6,6-difluoro-6,7-dihydro-2-[(4-methoxy-2-pyridyl)methylsulfinyl]-1H-[1,4]-dioxino[2,3-f]benzimidazole, 6,6-difluoro-6,7-dihydro-2-[(4-methoxy-3-methyl-2-pyridyl)methylthio]-1H-[1,4]-dioxino[2,3-f]benzimidazole, 6,6-difluoro-6,7-dihydro-2-[(4-methoxy-3-methyl-2-pyridyl)methylsulfinyl]-1H-[1,4]-dioxino[2,3-f]benzimidazole, 6,6-difluoro-6,7-dihydro-2-[(4-methoxy-5-methyl-2-pyridyl)methylthio]-1H-[1,4]-dioxino[2,3-f]benzimidazole, 6,6-difluoro-6,7-dihydro-2-[(4-methoxy-5-methyl-2-pyridyl)methylsulfinyl]-1H-[1,4]-dioxino[2,3f]benzimidazole, 6,6-difluoro-6,7-dihydro-2-[(4-methoxy-3,5-dimethyl-2-pyridyl)methylthio]-1H-[1,4]-dioxino[2,3-f]benzimidazole, 6,6-difluoro-6,7-dihydro-2-[(4-methoxy-3,5-dimethyl-2-pyridyl)methylsulfinyl]-1H-[1,4]-dioxino[2,3f]benzimidazole, 6,6-difluoro-6,7-dihydro-2-[(3-methyl-2-pyridyl)methylthio]-1H-[1,4]-dioxino[2,3-f]benzimidazole, 6,6-difluoro-6,7-dihydro-2-[(3-methyl-2-pyridyl)methylsulfinyl]-1H-[1,4]-dioxino[2,3-f]benzimidazole, 6,6,7,7-tetrafluoro-6,7-dihydro-2-[(4-methoxy-2-pyridyl)methylthio]-1H-[1,4]-dioxino[2,3f]benzimidazole, 6,6,7,7-tetrafluoro-6,7-dihydro-2-[(4-methoxy-2-pyridyl)methylsulfinyl]-1H-[1,4]-dioxino[2,3-f]benzimidazole, 6,6,7,7-tetrafluoro-6,7-dihydro-2-[(4-methoxy-3-methyl-2-pyridyl)methylthio]-1H-[1,4]-dioxino[2,3-f]benzimidazole, 6,6,7,7-tetrafluoro-6,7-dihydro-2-[(4-methoxy-3-methyl-2-pyridyl)methylsulfinyl]-1H-[1,4]-dioxino[2,3-f]benzimidazole, 6,6,7,7-tetrafluoro-6,7-dihydro-2-[(4-methoxy-5-methyl-2-pyridyl)methylthio]-1H-[1,4]-dioxino[2,3-f]benzimidazole, 6,6,7,7-tetrafluoro-6,7-dihydro-2-[(4-methoxy-5-methyl-2-pyridyl)methylsulfinyl]-1H-[1,4]-dioxino[2,3-f]benzimidazole, 6,6,7,7-tetrafluoro-6,7-dihydro-2-[(4-methoxy-3,5-dimethyl-2-pyridyl)methylthio]-1H-[1,4]-dioxino[2,3-f]benzimidazole, 6,6,7,7-tetrafluoro-6,7-dihydro-2-[(4-methoxy-3,5-dimethyl-2-pyridyl)methylsulfinyl]-1H-[1,4]-dioxino[2,3-f]benzimidazole, 6,6,7,7-tetrafluoro-6,7-dihydro-2-[(3-methyl-2-pyridyl)-methylthio]-1H-[1,4]-dioxino[2,3-f]benzimidazole, 6,6,7,7-tetrafluoro-6,7-dihydro-2-[(3-methyl-2-pyridyl)-methylsulfinyl]-1H-[1,4]-dioxino[2,3-f]benzimidazole, 6,6,8,8-tetrafluoro-1,8-dihydro-2-[(4-methoxy-2-pyridyl)methylthio]-[1,3]-dioxino[4,5-f]benzimidazole, 6,6,8,8-tetrafluoro-1,8-dihydro-2-[(4-methoxy-2-pyridyl)methylsulfinyl]-[1,3]-dioxino[4,5-f]benzimidazole, 6,6,8,8-tetrafluoro-1,8-dihydro-2-[(4-methoxy-3-methyl2-pyridyl)methylthio]-[1,3]-dioxino[4,5-f]benzimidazole, 6,6,8,8-tetrafluoro-1,8-dihydro-2-[(4-methoxy-3-methyl2-pyridyl)methylsulfinyl]-[1,3]-dioxino[4,5-f]benzimidazole, 6,6,8,8-tetrafluoro-1,8-dihydro-2-[(4-methoxy-5-methyl-2-pyridyl)methylthio]-[1,3]-dioxino[4,5-f]benzimidazole, 6,6,8,8-tetrafluoro-1,8-dihydro-2-[(4-methoxy-5-methyl-2-pyridyl)methylsulfinyl]-[1,3]-dioxino[4,5-f]benzimidazole, 6,6,8,8-tetrafluoro-1,8-dihydro-2-[(3-methyl-2-pyridyl)-methylthio]-[1,3]-dioxino[4,5-f]benzimidazole, 6,6,8,8-tetrafluoro-1,8-dihydro-2-[(3-methyl-2-pyridyl)-methylsulfinyl]-[1,3]-dioxino[4,5-f]benzimidazole, 6-chloro-6,7,7-trifluoro-6,7-dihydro-2-[(4-methoxy-5-methyl-2-pyridyl)methylsulfinyl]-1H-[1,4]-dioxino[2,3-f]benzimidazole, 6-chloro-6,7,7-trifluoro-6,7-dihydro-2-[(4-methoxy-5-methyl-2-pyridyl)methylthio]-1H-[1,4]-dioxino[2,3-f]benzimidazole, 6-chloro-6,7,7-trifluoro-6,7-dihydro-2-[(4-methoxy-3,5-dimethyl-2-pyridyl)methylsulfinyl]-1H-[1,4]-dioxino[2,3-f]benzimidazole, 6-chloro-6,7,7-trifluoro-6,7-dihydro-2-[(4-methoxy-3,5-dimethyl-2-pyridyl)methylthio]-1H-[1,4]-dioxino[2,3-f]benzimidazole, and their salts.

Because of tautomerism in the imidazole ring of the tricyclic radical, in compounds in which R is a bond and R1 represents a substituted ethylene radical, the 6-position in the [1,4]-dioxino-[2,3-f]benzimidazole part is identical to the 7-position. In compounds in which R and R1 represent a difluoromethylene radical, the 6-position in the [1,3]-dioxino[4,5-f]benzimidazole part is identical to the 7-position, and the 5-position is identical to the 8-position.

The invention furthermore relates to a process for the preparation of the tricyclic ethers of the formula I, wherein R, R1, R2, R3, R4 and n have their previously-ascribed meanings, and their salts.

The process is characterized in that (a) mercaptobenzimidazoles of formula II are reacted with picoline derivatives III

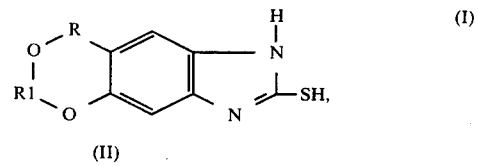

(II)

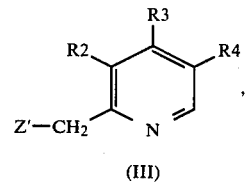

(III)

or (b) benzimidazoles of formula IV are reacted with mercaptopicolines V

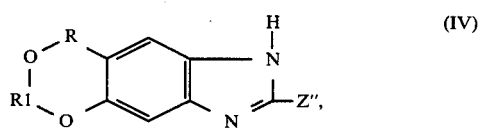

(IV)

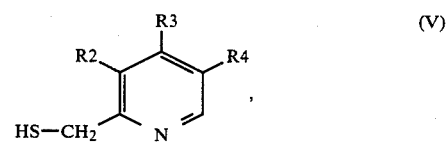

(V)

or (c) o-phenylenediamines of formula VI are reacted with formic acid derivatives VII

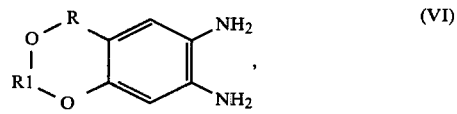

(VI)

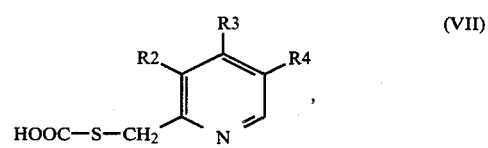

(VII)

and, when appropriate, the 2-benzimidazolyl 2-pyridyl sulfides obtained according to (a), (b) or (c), of formula VIII

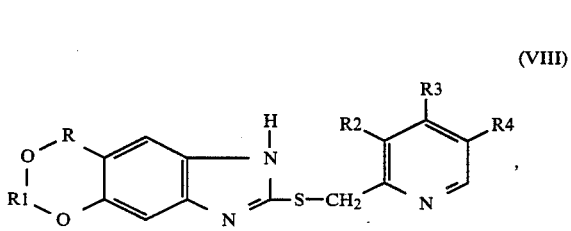

(VIII)

are then oxidized and/or converted into the salts, or in that (d) benzimidazoles of formula IX are reacted with pyridine derivatives X

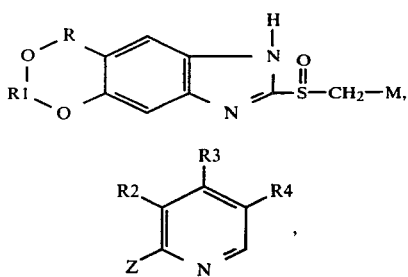

or (e) sulfinyl derivatives of formula XI are reacted with 2-picoline derivatives XII

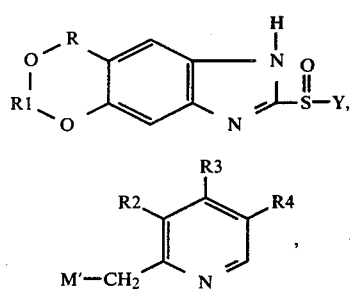

and, when appropriate, the products are then converted into salts, Y, Z, Z' and Z" representing suitable leaving groups, M representing an alkali metal atom (Li, Na or K), M' representing the equivalent of a metal atom and R, R1, R2, R3, R4 and n having the abovementioned meanings.

In the described reactions, the compounds II-XII are used as such or, when appropriate, in the form of their salts.

Preparation processes (a), (b) and (c) lead to sulfides according to the invention, and oxidation of the compounds VIII and processes (d) and (e) yield sulfoxides according to the invention.

The expert is familiar with which leaving groups Y, Z, Z' and Z" are suitable, on the basis of his expert knowledge. A suitable leaving group Y is, for example, a group which forms a reactive sulfinic acid derivative together with the sulfinyl group to which it is bonded. Examples of suitable leaving groups Y are alkoxy, dialkylamino and alkylmercapto groups. Examples of suitable leaving groups Z, Z' and Z" are halogen atoms, in particular chlorine atoms, or hydroxyl groups activated by esterification (for example with p-toluenesulfonic acid). The equivalent of a metal atom M' is, for example, an alkali metal atom (Li, Na or K) or an alkaline earth metal atom (for example Mg), which is substituted by a halogen atom (for example Br, Grignard reagent), or any other optionally substituted metal atom which is known to react like the abovementioned metals in substitution reactions of organometallic compounds.

The reaction of II with III is carried out in a manner which is known per se in suitable solvents, preferably polar protic or aprotic solvents (such as methanol, isopropanol, dimethylsulfoxide, acetone, dimethylformamide or acetonitrile), with addition or in the absence of water. It is carried out, for example, in the presence of a proton acceptor. Suitable proton acceptors are alkali metal hydroxides, such as sodium hydroxide, alkali metal carbonates, such as potassium carbonate, or tertiary amines, such as pyridine, triethylamine or ethyldiisopropylamine. Alternatively, the reaction is carried out without proton acceptors, in which case—depending on the nature of the starting compounds—an acid addition salt is optionally separated off initially in a particularly pure form. The reaction temperature is, e.g., between 0° and 150° C., preferred temperatures being between 20° C. and 80° C., in the presence of proton acceptors, and between 60° and 120° C. without proton acceptors—and in particular the boiling point of the solvents used. The reaction times are between 0.5 and 12 hours.

Similar reaction conditions to those for the reaction of II with III are used in the reaction of IV with V, which is carried out in a manner which is known per se.

The reaction of VI with VII is preferably carried out in polar, optionally water-containing solvents in the presence of a strong acid, for example hydrochloric acid, in particular at the boiling point of the solvent used.

The sulfides VIII are oxidized in a manner which is known per se under conditions with which the expert is familiar for the oxidation of sulfides to sulfoxides [in this context, see, for example, J. Drabowicz and M. Mikolajczyk, Organic preparations and procedures int. 14(1-2), 45-89 (1982) or E. Block in S.Patai, The Chemistry of Functional Groups, Supplement E, Part 1, pages 539-608, John Wiley and Sons (Interscience Publication), 1980]. Possible oxidizing agents are all the reagents usually employed for the oxidation of sulfides, in particular peroxyacids, such as, peroxyacetic acid, trifluoroperoxyacetic acid, 3,5-dinitroperoxybenzoic acid, peroxymaleic acid or, preferably, m-chloroperoxybenzoic acid.

The reaction temperature is between −70° C. and the boiling point of the solvent used (depending on the reactivity of the oxidizing agent and the degree of dilution), but is preferably between −30° C. and +20° C. Oxidation with halogens or with hypohalites (for example with aqueous sodium hypochlorite solution) has also proved advantageous, and is appropriately carried out at temperatures between 0° C. and 30° C. The reaction is advantageously carried out in inert solvents, for example aromatic or chlorinated hydrocarbons, such as benzene, toluene, methylene chlorid or chloroform, preferably in esters, such as ethyl acetate or isopropyl acetate, or ethers, such as dioxane.

The reaction of IX with X is preferably carried out in inert solvents, such as those which are also usually employed for the reaction of enolate ions with alkylating agents. Examples are aromatic solvents, such as benzene or toluene. The reaction temperature is as a rule between 0° and 120° C. (depending on the nature of the alkali metal atom M and the leaving group Z), the boiling point of the solvent used being preferred. For example [when M represents Li (lithium) and Z represents Cl (chlorine) and the reaction is carried out in benzene], the boiling point of benzene (80° C.) is preferred.

Compounds XI are reacted with compounds XII in a manner which is known per se, such as that with which the expert is familiar for the reaction of organometallic compounds.

Compounds according to the invention are first obtained either as such or in the form of their salts, depending on the nature of the starting compounds, which are also employed, when appropriate, in the form of their salts, and depending on reaction conditions.

The salts are otherwise obtained by dissolving obtained free compounds in a suitable solvent, for example in a chlorinated hydrocarbon, such as methylene chloride or chloroform, a low-molecular aliphatic alcohol (ethanol or isopropanol), an ether (diisopropyl ether), a ketone (acetone), or water, which contains the desired acid or base or to which the desired acid or base—when appropriate in the exactly calculated stoichiometric amount—is then added.

The salts are isolated by filtration, reprecipitation or precipitation or by evaporation of the solvent.

Obtained salts are readily converted into a corresponding free compound by alkalization or acidification, for example with aqueous sodium bicarbonate or with dilute hydrochloric acid, and free compounds are, in turn, converted into salts. In this manner, the compounds are purified or pharmacologically unacceptable salts are converted into pharmacologically acceptable salts.

The sulfoxides according to the invention are optically active compounds. The invention thus relates both to the enantiomers and to their mixtures and racemates. The enantiomers are separated in a manner which is known per se (for example by preparation and separation of corresponding diastereomeric compounds). However, the enantiomers are also prepared by asymmetric synthesis, for example by reacting optically active pure compounds XI or diastereomeric pure compounds XI with compounds XII [in this context, see K. K. Andersen, Tetrahedron Lett., 93 (1962)].

The compounds according to the invention are preferably synthesized by reaction of II with III and, when appropriate, subsequent oxidation of the sulfide VIII formed.

Compounds of formula II are new and are likewise the subject of the invention. Compounds III–VII and IX–XII are either known or are readily prepared analogously to known compounds from available starting materials. Compounds II are obtained, for example, by reacting compounds VI with carbon disulfide in the presence of alkali metal hydroxides or with alkali metal O-ethyldithiocarbonates. Compounds III are prepared by the method of O. E. Schulz and S. Fedders, Arch. Pharm. (Weinheim) 310, 128–136 (1977).

Compounds VI are synthesized by the general preparation method represented by the following reaction scheme:

Reaction scheme:

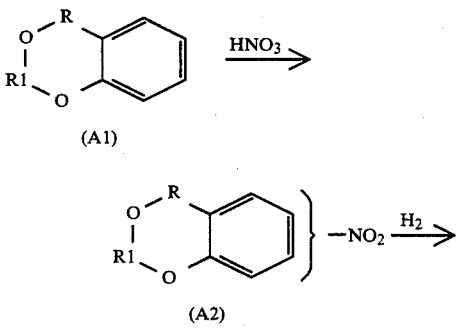

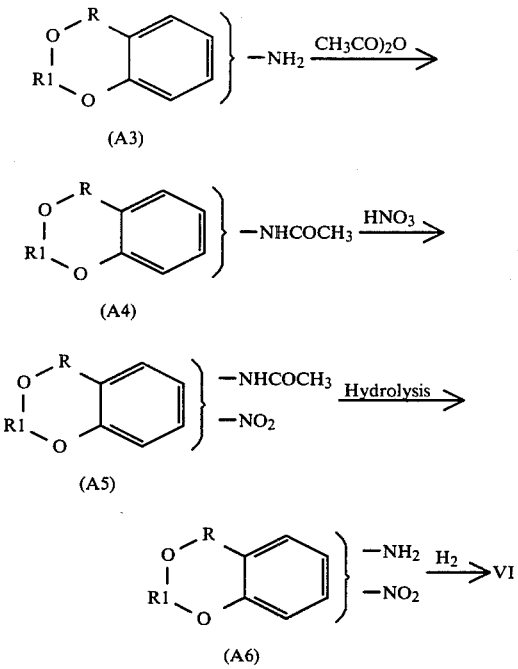

Starting compounds A1–A6 are prepared by known methods or analogy processes [for example German Offenlegungsschrift 28 48 531; C.A. 60, 13352 h (1964); and Liebigs Ann. Chem. 730, 16–30 (1969)], whereby isomer mixtures may be intermediately formed.

Compounds IX are obtained, for example, from compounds II by methylation, oxidation and subsequent deprotonation—for example with alkali metal hydroxides or alcoholates or customary organometallic compounds. Compounds X are prepared by the method of Z. Talik, Roczniki Chem. 35, 475 (1961).

The following examples illustrate the invention in more detail without limiting it. m.p. denotes melting point, the abbrevation h is used for hour(s) and the abbreviation min. is used for minutes. "Ether" is understood as meaning diethyl ether.

EXAMPLES 1. 2,2-Difluoro-6-[(4-methoxy-2-pyridyl)methylsulfinyl]-5H-[1,3]-dioxolo[4,5-f]benzimidazole A solution of 0.91 g of approximately 85% pure m-chloroperoxybenzoic acid in 20 ml of methylene chloride is added dropwise to a solution of 1.5 g of 2,2-difluoro-6-[(4-methoxy-2-pyridyl)methylthio]-5H-[1,3]-dioxolo[4,5-f]benzimidazole in 50 ml of methylene chloride at −30° C. in the course of 5 min., with stirring, and the temperature is allowed to rise to −10° C. in the course of 30 min. 0.62 ml of triethylamine is added, followed by 20 ml of aqueous potassium bicarbonate solution, the title compound already crystallizing out in the cold. The mixture is filtered and the precipitate is washed with water to yield 1.2 g of the title compound. The organic phase is separated off from the filtrate, washed with water and dried with magnesium sulfate and the solution is concentrated completely, at 30° C. A further 0.25 g of the title compound is obtained from the residue by recrystallization from ethyl acetate; total yield: 92%, m.p.: 184°–185° C. (decompositon).

The following compounds are obtained analogously:

2,2-difluoro-6-[(4-methoxy-3-methyl-2-pyridyl)methylsulfinyl]-5H-[1,3]-dioxolo-[4,5-f]benzimidazole of m.p.: 196°-197° C. (decompositon) from ethyl acetate, in 88% yield, 2,2-difluoro-6-[(4-methoxy-5-methyl-2-pyridyl)methylsulfinyl]-5H-[1,3]-dioxolo[4,5-f]benzimidazole of m.p.: 188°-189° C. (decompositon) from ethyl acetate, in 86% yield, and 2,2-difluoro-6-[(4-methoxy-3,5-dimethyl-2-pyridyl)methylsulfinyl]-5H-[1,3]-dioxolo[4,5-f]benzimidazole of m.p.: 196°-198° C. (decompositon) from toluene, in 90% yield by reacting 2,2-difluoro-6-[(4-methoxy-3-methyl-2-pyridyl)methylthio]-5H-[1,3]-dioxolo[4,5-f]benzimidazole, 2,2-difluoro-6-[(4-methoxy-5-methyl-2-pyridyl)methylthio]-5H-[1,3]-dioxolo[4,5-f]benzimidazole and 2,2-difluoro-6-[(4-methoxy-3,5-dimethyl-2-pyridyl)methylthio]-5H-[1,3]-dioxolo[4,5-f]benzimidazole with m-chloroperoxybenzoic acid.

2.

2,2-Difluoro-6-[(4-methoxy-5-methyl-2-pyridyl)methylsulfinyl]-5H-[1,3-]-dioxolo[4,5-f]benzimidazole A mixture of 8 ml commercially available sodium hypochlorite solution (about 15% of active chlorine) and 5 ml of 10% strength sodium hydroxide solution is added dropwise to a suspension of 1.5 g of 2,2-difluoro-6-[(4-methoxy-5-methyl-2-pyridyl)methylthio]-5H-[1,3-]-dioxolo[4,5-f]benzimidazole in 60 ml of ethyl acetate at 0° C. in the course of 20 min., and stirring is continued at 0° C. for 15 min. 0.5 ml of 10% strength sodium thiosulfate solution and 1.3 g of ammonium sulfate are added, the organic phase is separated off and washed with water, the solution is concentrated in vacuo at 30° C. and the residue is crystallized from ethyl acetate. 1.2 g (74%) of the title compound of m.p. 175°-176° C. (decomposition) are obtained.

The following compound is obtained analogously: 2,2-difluoro-6-[(3-methyl-2-pyridyl)methylsulfinyl]-5H-[1,3-]-dioxolo[4,5-f]benzimidazole of m.p. 196°-197° C. (decomposition; from ethyl acetate), in 78% yield, by oxidation of 2,2-difluoro-6-[(3-methyl-2-pyridyl)methylthio]-5H-[1,3-]-dioxolo-[4,5-f]benzimidazole witth sodium hypochlorite solution.

3.

2,2-Difluoro-6-[(4-methoxy-2-pyridyl)methylthio]-5H-[1,3-]-dioxolo[4,5-f]benzimidazole 3.5 g of 2,2-difluoro-5H-[1,3-]-dioxolo[4,5-f]benzimidazole-6-thiol and 3.3 g of 2-chloromethyl-4-methoxypyridine hydrochloride are heated at the boiling point under reflux in 150 ml of isopropanol for 5 h. The mixture is filtered at room temperature and 6.2 g (97%) of the dihydrochloride of the title compound are obtained. The salt is dissolved in hot water, the solution is clarified with active charcoal and the base is liberated with potassium bicarbonate solution. 5.0 g (94%) of the title compound of m.p. 151°-152° C. (from toluene) are obtained.

The following compounds are obtained by an analogous reaction with the hydrochlorides of 2-chloromethyl-4-methoxy-3-methylpyridine, 2-chloromethyl-4-methoxy-5-methyl-pyridine, 2-chloromethyl-3-methylpyridine, 2-chloromethyl-5-methylpyridine and 2-chloromethylpyridine:

2,2-difluoro-6-[(4-methoxy-3-methyl-2-pyridyl)methylthio]-5H-[1,3]-dioxolo[4,5-f]benzimidazole (m.p. 213°-214° C.), in 82% yield, 2,2-difluoro-6-[(4-methoxy-5-methyl-2-pyridyl)methylthio]-5H-[1,3]-dioxolo[4,5-f]benzimidazole (m.p. 192°-193° C.), in 88% yield, 2,2-difluoro-6-[(3-methyl-2-pyridyl)methylthio]-5H-[1,3]-dioxolo[4,5-f]benzimidazole (m.p. 174°-175° C.), in 94% yield, 2,2-difluoro-6-[(5-methyl-2-pyridyl)methylthio]-5H-[1,3]-dioxolo[4,5-f]benzimidazole (m.p. 190°-191° C.), in 75% yield and 2,2-difluoro-6-[(2-pyridyl)methylthio]-5H-[1,3]-dioxolo[4,5-f]benzimidazole (m.p. 176°-177° C.), in 94% yield.

4.

2,2-Difluoro-5H-[1,3]-dioxolo[4,5-f]benzimidazole-6-thiol (a) 30 g of 4-amino-2,2-difluoro-5-nitro-1,3-benzodioxole are hydrogenated in 300 ml of methanol on 0.5 g of 10% strength palladium-on-charcoal in a circulatory hydrogenation apparatus under atmospheric pressure and at room temperature, 2.5 equivalents of methanolic hydrogen chloride solution are added, the mixture is filtered, the solution is concentrated in vacuo and isopropanol and ether are added to the residue to give 35 g (97%) of 2,2-difluoro-1,3-benzodioxole-4,5-diamine dihydrochloride of m.p. 232°-233° C. (decomposition).

(b) 24 g of potassium O-ethyldithiocarbonate (recrystallized from isopropanol) and 9.2 g of sodium hydroxide in 55 ml of water are added to 30 g of the compound from (a) in 300 ml of ethanol and the mixture is heated at the boiling point under reflux for 15 h. The mixture is poured onto 1.5 liters of water, adjusted to pH 14 with sodium hydroxide solution, clarified with active charcoal and precipitated with concentrated hydrochloric acid under the influence of heat, and the precipitate is filtered off with suction, in the cold. 24 g (91%) of the title compound of m.p. 365°-370° C. (decomposition) are obtained.

5.

6,6,7-Trifluoro-6,7-dihydro-2-[(4-methoxy-2-pyridyl)-methylsulfinyl]-1H-[1,4]-dioxino[2,3-f]benzimidazole A solution of 0.81 g of approximately 85% pure m-chloroperoxybenzoic acid in 20 ml of ethyl acetate is added dropwise to a solution of 1.5 g of 6,6,7-trifluoro-6,7-dihydro-2-[(4-methoxy-2-pyridyl)methylthio]-1H-[1,4]-dioxino[2,3-f]benzimidazole in 50 ml of methylene chloride at −20° C. to −15° C. in the course of 30 min., with stirring, and stirring is continued at this temperature for 30 min. 0.66 ml of triethylamine is added and the organic solution is washed with 1M potassium bicarbonate solution and then with water, dried with magnesium sulfate and concentrated in vacuo. The residue is allowed to crystallize from ether. 1.2 g (77%) of the title compound of m.p. 166°-167° C. (decomposition), from ethyl acetate, are obtained.

The following compounds are obtained analogously:
6,6,7-trifluoro-6,7-dihydro-2-[(4-methoxy-3-methyl-2-pyridyl)methylsulfinyl]-1H-[1,4]-dioxino[2,3-f]benzimidazole, of m.p. 185°-186° C. (decomposition; from ethyl acetate and 3-pentanone), in 76% yield, 6,6,7-trifluoro-6,7-dihydro-2-[(4-methoxy-3,5-dimethyl-2-pyridyl)methylsulfinyl]-1H-[1,4]-dioxino[2,3-f]benzimidazole, of m.p. 181°-182° C. (decomposition; from ethyl acetate), in 60% yield, and 6,6,7-trifluoro-6,7-dihydro-2-[(4-methoxy-5-methyl-2-pyridyl)methylsulfinyl]-1H-[1,4]-dioxino2,3-f]benzimidazole, of m.p. 177°–179° C. (decomposition; from ethyl acetate), in 47% yield
by oxidation of
6,6,7-trifluoro-6,7-dihydro-2-[(4-methoxy-3-methyl-2-pyridyl)methylthio]-1H-[1,4]-dioxino[2,3-f]benzimidazole,
6,6,7-trifluoro-6,7-dihydro-2-[(4-methoxy-3,5-dimethyl-2-pyridyl)methylthio]-1H-[1,4]-dioxino[2,3-f]benzimidazole, and
6,6,7-trifluoro-6,7-dihydro-2-[(4-methoxy-5-methyl-2-pyridyl)methylthio]-1H-[1,4]-dioxino[2,3-f]benzimidazole
with m-chloroperoxybenzoic acid.

6.

6,6,7-Trifluoro-6,7-dihydro-2-[(5-methyl-2-pyridyl)methylsulfinyl]-1H-[1,4]-dioxino[2,3-f]benzimidazole 2.4 ml of 2M sodium hydroxide solution and 0.8 ml of water are added to a solution of 1.75 g of 6,6,7-trifluoro-6,7-dihydro-2-[(5-methyl-2-pyridyl)methylthio]-1H-[1,4]-dioxino[2,3-f]benzimidazole in 18 ml of dioxane. A mixture of 4.6 ml of sodium hypochlorite solution (8.9 g of active chlorine per ml) and 2.9 ml of 2M sodium hydroxide solution is added to the above solution at 30° C. in the course of 15 min. The mixture is stirred at 30° C. for 50 min., some drops of 2M sodium dithionite solution are added and the solution is concentrated in vacuo. 100 ml of water and 20 ml of ethyl acetate are added to the residue, and the title compound (1.6 g, 87% yield of m.p. 186°–187° C.) is precipitated by addition of sodium dihydrogen phosphate solution up to pH 7.

2,2-Difluoro-6-[(5-methyl-2-pyridyl)methylsulfinyl]-5H-[1,3]-dioxolo-[4,5-f]benzimidazole of m.p. 206°–208° C. (decompostion) are obtained analogously in 93% yield.

7.

6,6,7-Trifluoro-6,7-dihydro-2-[(4-methoxy-2-pyridyl)methylthio]-1H-[1,4]-dioxino[2,3-f]benzimidazole 3.0 g of 6,6,7-trifluoro-6,7-dihydro-1H-[1,4]-dioxino-2,3-f]benzimidazole-2-thiol and 2.4 g of 2-chloromethyl-4-methoxypyridine hydrochloride in 60 ml of isopropanol are heated at the boiling point under reflux for 4.5 h and half of the solvent is distilled off. 4.8 g (92%) of the dihydrochloride of the title compound of m.p. 218°–220° C. (decomposition) are obtained. The salt is dissolved in hot water and the solution is clarified with active charcoal, rendered alkaline with 1M potassium bicarbonate solution and extracted by shaking with methylene chloride. The organic phase is washed with water, dried with magnesium sulfate and concentrated in vacuo. The residue is allowed to crystallize from ether to give 3.7 g (84%) of the title compound of m.p. 139°–140° C.

Analogous reaction with the hydrochlorides of 2-chloromethyl-4-methoxy-3-methylpyridine, 2-chloromethyl-4-methoxy-5-methylpyridine and 2-chloromethyl-5-methylpyridine gives
6,6,7-trifluoro-6,7-dihydro-2-[(4-methoxy-3-methyl-2-pyridyl)methylthio]-1H-[1,4]-dioxino[2,3-f]benzimidazole, of m.p. 213°–214° C., in 75% yield (dihydrochloride: m.p. 210°–211° C.),
6,6,7-trifluoro-6,7-dihydro-2-[(4-methoxy-5-methyl-2-pyridyl)methylthio]-1H-[1,4]-dioxino[2,3-f]benzimidazole, of m.p. 165°–167° C., in 73% yield and
6,6,7-trifluoro-6,7-dihydro-2-[(5-methyl-2-pyridyl)methylthio]-1H-[1,4]-dioxino[2,3-f]benzimidazole, of m.p. 144°–145° C. in 80% yield.

8.

6,6,7-Trifluoro-6,7-dihydro-2-[(4-methoxy-3,5-dimethyl-2-pyridyl]methylthio]-1H-[1,4]-dioxino[2,3-f]benzimidazole 6.1 ml of 2M sodium hydroxide solution are added dropwise to a mixture of 1.6 g of 6,6,7-trifluoro-6,7-dihydro-1H-[1,4]-dioxino[2,3-f]benzimidazole-2-thiol and 1.4 g of 2-chloromethyl-4-methoxy-3,5-dimethylpyridine hydrochloride in 40 ml of ethanol at room temperature and the mixture is stirred at 40° C. for 5 h. The solvent is distilled off in vacuo, water is added, the mixture is extracted with methylene chloride, the organic solution is concentrated and the residue is recrystallized from ethanol and water. 1.9 g (77%) of the title compound of m.p. 138°–140° C. are obtained.

Analogous reaction of 2,2-difluoro-5H-[1,3]-dioxolo[4,5-f]benzimidazole-6-thiol with 2-chloromethyl-4-methoxy-3,5-dimethylpyridine gives 2,2-difluoro-6-[(4-methoxy-3,5-dimethyl-2-pyridyl)methylthio]-5H-[1,3]-dioxolo[4,5-f]benzimidazole, of m.p. 148°–149° C. (from acetonitrile), in 86% yield.

9.

6-Chloro-6,7,7-trifluoro-6,7-dihydro-2-[(4-methoxy-3-methyl-2-pyridyl)methylsulfinyl]-1H-[1,4]-dioxino[2,3-f]benzimidazole A solution of 0.42 g of approximately 85% pure m-chloroperoxybenzoic acid in 90 ml of methylene chloride is added dropwise to a solution of 0.9 g of 6-chloro-6,7,7-trifluoro-6,7-dihydro-2-[(4-methoxy-3-methyl-2-pyridyl)methylthio]-1H-[1,4]-dioxino[2,3-f]benzimidazole in 180 ml of methylene chloride at −40° C., with stirring. Stirring is continued for 4 hours and the solution is allowed to come to −20° C. 0.29 ml of trimethyl amine are added, and the organic phase is washed with potassium bicarbonate solution and with water, dried with magnesium sulfate and concentrated in vacuo. The residue is stirred with ethyl acetate and subsequently with acetone. 0.6 g (64%) of the title compound of m.p. 198°–200° C. (decomposition) are obtained.

Analogously 6-chloro-6,7,7-trifluoro-6,7-dihydro-2-[(4-methoxy-2-pyridyl)methylsulfinyl]-1H-[1,4]-dioxino[2,3-f]benzimidazole of m.p. 179°–181° C. (decomposition; from ethyl acetate), is obtained by oxidation of
6-chloro-6,7,7-trifluoro-6,7-dihydro-2-[(4-methoxy-2-pyridyl)methylthio]-1H-[1,4]-dioxino[2,3-f]benzimidazole with m-chloroperoxybenzoic acid.
Analogously to Example 7
6-chloro-6,7,7-trifluoro-6,7-dihydro-2-[(4-methoxy-3-methyl-2-pyridyl)methylthio]-1H-[1,4]-dioxino[2,3-f]benzimidazole of m.p. 193°–195° C. (from toluene) and
6-chloro-6,7,7-trifluoro-6,7-dihydro-2-[(4-methoxy-2-pyridyl)methylthio]-1H-[1,4]-dioxino[2,3-f]benzimidazole of m.p. 178°–180° C. (from toluene)
are obtained by reaction of
6-chloro-6,7,7-trifluoro-6,7-dihydro-1H-[1,4]-dioxino[2,3-f]benzimidazole-2-thiol with 2-chloromethyl-4-methoxy-3-methylpyridine and 2-chloromethyl-4-methoxypyridine.

10.

6,6,7-Trifluoro-6,7-dihydro-1H-[1,4]-dioxino[2,3-f]benzimidazole-2-thiol (a) A mixture of 39.5 ml of 69% strength nitric acid and 46 ml of 97% strength sulfuric acid is added dropwise to 50 g of 2,2,3-trifluoro-2,3-dihydro-1,4-benzodioxine at 5° C. in the course of 1 h. The mixture is stirred at 10° C. for 1 h, at 20° C. for 1 h and at 40° C. for 5 min., poured onto 200 g of ice and extracted with methylene chloride and the extract is washed with water, dried with magnesium sulfate and distilled in vacuo. 58 g (94%) of a mixture of 2,3,3-trifluoro-2,3-dihydro-6-nitro-(and 7-nitro)-1,4-benzodioxine of b.p. 68.5° C. (0.15 mbar) and $n_D^{20}$ 1.5080 are obtained. A gas chromatogram with a 10 m fused silica column (Chrompack) shows two peaks in a ratio of 2:3.

(b) 35 g of the isomer mixture are hydrogenated in 400 ml of ethanol on 3 g of 10% strength palladium-on-charcoal under atmospheric pressure and at 20°–30° C. in a circulating hydrogenation apparatus, the mixture is filtered and the filtrate is concentrated in vacuo., 30.5 g (100%) of a liquid mixture of 6-amino-(and 7-amino)-2,2,3-trifluoro-2,3-dihydro-1,4-benzodioxine are obtained.

(c) A mixture of 15.3 g of acetic anhydride and 15 ml of glacial acetic acid is added dropwise to 28 g of the isomer mixture from (b) at 20°–30° C., the mixture is stirred at 30° C. for 30 min., 1 ml of water is added, the mixture is stirred at 30° C. for 30 min. and the solvent is distilled off in vacuo. 19 g of a fraction of the mixture of the isomeric acetamino derivatives of m.p. 128°–133° C. are obtained by recrystallization from toluene.

(d) 14 ml of 100% pure nitric acid, dissolved in 60 ml of methylene chloride, are added dropwise to 17 g of the isomer mixture of the acetamino derivatives [from (c)], suspended in 200 ml of methylene chloride, at −6° to −8° C. and the mixture is stirred at 0° C. for 2 h and then overnight at room temperature. The mixture is poured onto 110 g of ice and the organic phase is separated off, washed with water and concentrated in vacuo. The residue (19.8 g) is recrystallized from 20 ml of ethanol. 15.5 g of a mixture of 6-acetamino-2,2,3-trifluoro-2,3-dihydro-7-nitro-1,4-benzodioxine and 7-acetamino-2,2,3-trifluoro-2,3-dihydro-6-nitro-1,4-benzodioxine are obtained.

(e) 14.5 g of the product mixture from (d) are suspended in 80 ml of methanol, and 30 ml of 5M sodium hydroxide solution are added dropwise, the mixture being warmed to 30° C. Stirring is continued at room temperature for 0.5 h and the mixture is poured onto 200 g of ice to give 11.7 g of a mixture of 6-amino-2,2,3-trifluoro-2,3-dihydro-7-nitro-1,4-benzodioxine and 7-amino-2,2,3-trifluoro-2,3-dihydro-6-nitro-1,4-benzodioxine. A sample is separated into two pure isomers of melting points 110.5°–111.5° C. and 120°–121° C. on a silica gel column with cyclohexane/ethyl acetate (4:1), the NMR spectra of these isomers on a 60 MHz apparatus in deuterochloroform being virtually identical.

(f) 10.9 g of the isomer mixture from (e) are hydrogenated in 300 ml of methanol at room temperature and under atmospheric pressure on 1 g of 10% strength palladium-on-charcoal in the course of 2.5 h. 30 ml of 4M hydrogen chloride in methanol are added, the mixture is filtered, the filtrate is concentrated in vacuo and the residue is stirred with 100 ml of ether. 12.6 g (98%) of 2,2,3-trifluoro-2,3-dihydro-1,4-benzodioxine-6,7-diamine dihydrochloride (m.p. >250° C.) are obtained.

(g) 20.5 ml of 4M aqueous potassium hydroxide solution are added to 12 g of the compound from (f) and 8.5 g of potassium O-ethyldithiocarbonate (recrystallized from isopropanol) in 120 ml of ethanol and the mixture is heated at the boiling point under reflux for 17 h. The mixture is poured onto 300 g of ice, adjusted to pH 12–13 with potassium hydroxide solution, clarified with active charcoal and precipitated with concentrated hydrochloric acid. After renewed precipitation with acid from an alkaline aqueous-alcoholic solution, 10 g (93%) of the title compound of m.p. 309°–310° C. (decomposition) are obtained.

11.

6-Chloro-6,7,7-trifluoro-6,7-dihydro-1H-[1,4]-dioxino[2,3-f]benzimidazole-2-thiol (a) A mixture of 18.3 ml of 65% strength nitric acid and 15.4 ml of 97% strength sulfuric acid is added dropwise to 18 g of 2-chloro-2,3,3-trifluoro-2,3-dihydro-1,4-benzodioxine at 5° C. The mixture is stirred at 5°–10° C. for 2 h, poured onto ice and extracted with methylene chloride. 21.3 g of a mixture of 2-chloro-2,3,3-trifluoro-2,3-dihydro-6-nitro-(and 7-nitro)-1,4-benzodioxine are obtained as an oil.

(b) The compounds from (a) are reacted in accordance with the method of Example 10b to give an oily mixture of 2-chloro-2,3,3,-trifluoro-2,3-dihydro-1,4-benzodioxine-6-(and 7-)amino (95% yield), which is then reacted according to Example 10c to yield a mixture of the corresponding acetamino derivatives quantitatively.

(c) 19 g of the product mixture from (b) in 190 ml of methylene chloride are stirred with 16 ml of 100% pure nitric acid. The reaction product is purified by chromatography on a silica gel column with cyclohexane/ethyl acetate (4:1). 15 g of a mixture of 6-acetamino-2-chloro-2,3,3-trifluoro-6,7-dihydro-7-nitro-1,4-benzodioxine and 7-acetamino-2-chloro-2,3,3-trifluoro-6,7-dihydro-6-nitro-1,4-benzodioxine are obtained as a pale yellow oil.

(d) 10.2 ml of a 30% strength sodium methylate solution in methanol are added dropwise to 14.5 g of the product mixture from (c) in 100 ml of methanol at 5° C. Stirring is continued for one and a half hours without cooling and the mixture is poured onto ice, neutralised with diluted hydrochloric acid, extracted with methylene chloride and concentrated in vacuo. 12.7 g of a mixture of 6-amino-2-chloro-2,3,3-trifluoro-2,3-dihydro-7-nitro-1,4-benzodioxine and 7-amino-2-chloro-2,3,3-trifluoro-2,3-dihydro-6-nitro-1,4-benzodioxine are obtained as orange-coloured oil.

(e) 12.4 g of the product mixture from (d) are hydrogenated according to Example 10f. 12.6 g (99%) of 2-chloro-2,3,3-trifluoro-2,3-dihydro-1,4-benzodioxine-6,7-diamine dihydrochloride are obtained.

(f) 12.4 g of the compound from (e) are reacted with 9.1 g of potassium O-ethyldithiocarbonate and potassium hydroxide solution according to the method described in Example 10g. 9.6 g (74%) of the title compound of m.p. 288°–290° C. (decomposition) are obtained.

12.

2,2-Difluoro-6-[(4-methoxy-2-pyridyl)methylsulfinyl]-5H-[1,3]-dioxolo-[4,5-f]benzimidazole sodium salt A solution of 582 mg of sodium methylate in 2 ml of anhydrous methanol is added to a solution of 3.96 g of 2,2-difluoro-6-[(4-methoxy-2-pyridyl)methylsulfinyl]-

5H-[1,3]-dioxolo[4,5-f]benzimidazole in 30 ml of anhydrous methanol. After 15 min. the solution is concentrated in vacuo. The crystallizing residue is stirred for one hour with 60 ml of diethyl ether, is filtered off with suction, and is dried for 3 hours in a high-vacuum at 60° C. 4.1 g of the title compound (adduct with 1 mole of methanol) of m.p. 249° C. (decomposition) are obtained.

13. 2,2-Difluoro-6-[(4-methoxy-3-methyl-2-pyridyl)methylsulfinyl]-5H-[1,3]-dioxolo-[4,5-f]benzimidazole sodium salt 50 ml of 0.1M sodium hydroxide solution and 50 ml of acetone are added to 1.906 g of 2,2-difluoro-6-[(4-methoxy-3-methyl-2-pyridyl)methylsulfinyl]-5H-[1,3]-dioxolo[4,5-f]benzimidazole. The solution is concentrated in a rotatory evaporator at 60° C., the residue is crystallized by addition of diethyl ether, and dried in vacuo at 60° C. The title compound is obtained as hydrate.

14. 2-Chloromethyl-4-methoxypyridine hydrochloride 15 ml of thionyl chloride are added dropwise to a solution, cooled to −10° C., of 10 g (0.072 mole) of 2-hydroxymethyl-4-methoxypyridine in 30 ml of dry chloroform in the course of 15 minutes. The solution is allowed to come to room temperature and stirring is continued for one and a half hours. After the solvent and the excess thionyl chloride have been stripped off, colorless crystals are obtained, and these are recrystallized from isopropanol [12.1 g (87%), m.p. 149°–150° C., decomposition].

Analogously, reaction of 2-hydroxymethyl-4-methoxy-3-methylpyridine, 2-hydroxymethyl-4-methoxy-3,5-dimethylpyridine, 2-hydroxymethyl-4-methoxy-5-methylpyridine and 2-hydroxymethyl-3-methylpyridine with thionyl chloride gives 2-chloromethyl-4-methoxy-3-methylpyridine hydrochloride (m.p. 157°–158° C., decomposition, from isopropanol/ether), 2-chloromethyl-4-methoxy-3,5-dimethylpyridine hydrochloride [m.p. 135°–136° C. (decomposition) from isopropanol/ether], 2-chloromethyl-4-methoxy-5-methylpyridine hydrochloride [m.p. 147° C., (decomposition)] and 2-chloromethyl-3-methylpyridine hydrochloride (m.p. 163°–165° C.).

The 2-hydroxymethyl-pyridines (see also Example 15) are obtained in accordance with the method of or the instructions of O. E. Schulz and S. Fedders, Arch. Pharm. (Weinheim) 310, 128 (1977). The appropriately required intermediates are prepared in accordance with the method of H. C. Brown, S. Johnson and H. Podall, J.Am.Chem.Soc. 76, 5556 (1954).

15. 2-Hydroxymethyl-4-methoxy-3,5-dimethylpyridine hydrochloride 18 g of 2,3,5-trimethylpyridine [F. Bohlmann, A. Englisch, J. Politt, H. Sander and W. Weise, Chem. Ber. 88, 1831 (1955)] and 17 ml of 30% strength hydrogen peroxide are warmed at 100° C. in 80 ml of glacial acetic acid for 2.5 h. A further 10 ml of 30% strength hydrogen peroxide are then added and the temperature is maintained for a further 8 h. The mixture is subsequently concentrated to half the volume under a water-pump vacuum and is subjected to a peroxide test. When free from peroxide, all the solvent is stripped off in vacuo and the residue is distilled under a high vacuum. 19.2 g (95%) of 2,3,5-trimethylpyridine N-oxide pass over at 95°–98° C. under 1.33 Pa.

5.0 g of this product are dissolved in a mixture of 7 ml of fuming nitric acid and 7 ml of concentrated sulfuric acid at room temperature and the solution is warmed at a bath temperature of 40° C. for 18 hours. Thereafter, it is poured onto ice-water and rendered alkaline with concentrated sodium hydroxide solution, with cooling. Extraction of the mixture with ethyl acetate and removal of the solvent in vacuo gives crude 2,3,5-trimethyl-4-nitropyridine N-oxide, which is dissolved in 20 ml of dry methanol without further purification. 4.7 ml of commerically available 30% strength sodium methoxide in methanol are added to this solution and the mixture is warmed at 50° C. for 12 h. Thereafter, the solvent is stripped off; the residue is taken up in a little water and the mixture is extracted with ethyl acetate. After the solvent has been stripped off, the crude 4-methoxy-2,3,5-trimethylpyridine N-oxide which remains as an oil, is poured, without further purification, into 20 ml of hot acetic anhydride at 100° C. and is warmed at this temperature for 1 hour. Thereafter, the mixture is concentrated in vacuo, the residue is taken up, without futher purification, in 20 ml of 10% strength aqueous hydrochloric acid and the mixture is stirred at 50° C. for 2.5 h. It is concentrated to half the volume in vacuo, rendered alkaline with potassium carbonate and extracted with ethyl acetate. The combined extracts are dried over sodium sulfate; the solvent is stripped off in vacuo. The oily residue is dissolved in 50 ml of ethyl methyl ketone, and ethereal hydrochloric acid is added until precipitation is quantitative. The precipitate is recrystallized from dioxane with a little isopropanol. 3.1 g of the title compound of m.p. 126° C. are obtained. After chromatography of the free base on a silica gel column, an m.p. of 49°–51° C. is found for the free base and, after reprecipitation in hydrogen chloride/ether, an m.p. of 133.5° C. (decomposition) is found for the hydrochloride.

2-Hydroxymethyl-4-methoxy-5-methylpyridine (m.p. 102°–104° C.) is obtained in a similar manner.

COMMERCIAL USEFULNESS

The tricyclic ethers of formula I and their salts have useful pharmacological properties which render them commerically useful. They significantly inhibit the secretion of gastric acid in warm-blooded animals and moreover have an excellent protective effect on the stomach and intestines in warm-blooded animals. This protective effect on the stomach and intestine is observed even when doses below (less than) acid secretion-inhibiting doses are administered. Furthermore the compounds according to the invention are characterized by an absence of significant side-effects and an advantageous therapeutic range.

In this context, "protection of the stomach and intestines" means the prevention and treatment of gastrointestinal diseases, in particular gastrointestinal inflammatory diseases and lesions (such as gastric ulcer, duodenal ulcer, gastritis, hyperacid stomach irritation or stomach irritation caused by medicaments), which are caused, for example, by microorganisms, bacterial toxins, medicaments (for example certain antiphlogistics and antirheumatics), chemicals (for example ethanol), gastric acid or stress situations.

A further advantage of the compounds according to the invention is their comparatively high chemical stability.

Surprisingly, the excellent properties of the compounds according to the invention prove to be significantly superior to those of known prior art compounds. On the basis of these properties, the tricyclic ethers and their pharmacologically acceptable salts are outstandingly suitable for use in human and veterinary medicine, and they are particularly useful for the treatment and prophylaxis of diseases of the stomach and intestines and those diseases based on excessive secretion of gastric acid.

The invention thus furthermore relates to the compounds according to the invention for use in the treatment and prophylaxis of the mentioned diseases.

The invention also relates to the use of the compounds according to the invention in the preparation of medicaments which are used for the treatment and prophylaxis of the mentioned diseases.

The invention furthermore relates to medicaments which contain one or more tricyclic ethers of formula I and/or their pharmacologically acceptable salts.

The medicaments are prepared by processes which are known per se and with which the expert is familiar. As medicaments, the pharmacologically active compounds (=active substances) according to the invention are used either as such or, preferably, in combination with suitable pharmaceutical auxiliaries, in the form of tablets, coated tablets, capsules, suppositories, emulsions, suspensions or solutions, the content of active substance advantageously being between 0.1 and 95%.

The expert is familiar with the auxiliaries which are suitable for the desired medicament formulations, on the basis of his expert knowledge. Besides solvents, gel-forming agents, suppository bases, tablet auxiliaries and other active substance carriers, optional composition components include, for example, antioxidants, dispersing agents, emulsifiers, anti-foaming agents, flavor-correcting agents, preservatives, solubilizing agents, colorants and, in particular, percutaneous absorption promotors and complexing agents (e.g. cyclodextrins).

The active substances can be administered orally, parenterally or percutaneously.

In general, it has proved advantageous in human medicine to administer the active compound or compounds, in the case of oral administration, in a daily dose of from about 0.01 to about 20, preferably from 0.05 to 5 and in particular from 0.1 to 1.5 mg/kg of body weight, if necessary in the form of several, preferably 1 to 4, individual doses, in order to achieve the desired result. Similar or (especially in the case of intravenous administration of the active substances) as a rule lower dosages can be used for parenteral treatment. The particular optimum dosage required and the mode of administration of the active substances is easily determined by any expert on the basis of his expert knowledge.

When the compounds according to the invention and/or their salts are used for the treatment of the mentioned diseases, the pharmaceutical formulations optionally contain one or more pharmacologically active constituents from other groups of medicaments, such as antacids, for example aluminum hydroxide and magnesium aluminate; tranquilizers, such as benzodiazepines, for example diazepam; spasmolytic agents, such as bietamiverine and camylofin; anticholinergic agents, such as oxyphencyclimine and phencarbamide; local anesthetics, such as tetracaine and procaine; and, when appropriate, also enzymes, vitamines or aminoacids.

The active substances are formulated, for example, in the following manner:

(a) Tablets containing 40 mg of active substance 20 kg of 6,6,7-trifluoro-6,7-dihydro-2-[(4-methoxy-2-pyridyl)methylthio]-1H-[1,4]-dioxino[2,3-f]benzimidazole, 40 kg of lactose, 26 kg of maize starch and 3 kg of polyvinylpyrrolidone are moistened with about 20 liters of water and the mixture is granulated through a sieve of 1.25 mm mesh width. The granules are dried in a fluidized bed drier to a relative moisture of 50–60%, and 8 kg of sodium carboxymethylcellulose, 2 kg of talc and 1 kg of magnesium stearate are then added. The finished granules are pressed to tablets weighing 200 mg and having 8 mm in diameter.

(b) Capsules containing 30 mg of active substance 300 g of 6,6,7-trifluoro-6,7-dihydro-2-[(4-methoxy-3-methyl-2-pyridyl)methylsulfinyl]-1H-[1,4]-dioxino[2,3-f]benzimidazole, 695 g of microcrystalline cellulose and 5 g of amorphous silicic acid are finely powdered and mixed thoroughly and size 4 hard gelatin capsules are filled with the mixture.

(c) Capsules containing 10 mg of active substance 100 g of 2,2-difluoro-6-[(4-methoxy-2-pyridyl)methylsulfinyl]-5H-[1,3]-dioxolo[4,5-f]benzimidazole, 895 g of microcrystalline cellulose and 5 g of amorphous silicic acid are finely powdered and mixed thoroughly and size 4 hard gelatin capsules are filled with the mixture.

(d) Ampoules containing 10 mg of active substance 3.18 g of 2,2-difluoro-6-[(4-methoxy-2-pyridyl)methylsulfinyl]-5H-[1,3]-dioxolo[4,5-f]benzimidazole sodium salt are dissolved in a solution of 0.5 g of sodium carbonate and 165.5 g of mannitol in 1300 ml of distilled water, with stirring. The resulting solution is made up to 1500 ml with distilled water and sterile-filtered. In each case 5 ml of this solution are metered into a 15 ml vial and lyophilized. The lyophilizate can be reconstituted with 10 ml of water.

PHARMACOLOGY

The excellent protective effect on the stomach and the gastric secretion-inhibiting action of the tricyclic ethers according to the invention is demonstrated in animal experiments using the Shay rat model. In these experiments, the compounds according to the invention were compared with prior art compounds (A–D) of UK Patent Application GB No. 2 082 580. The compounds investigated are numbered as follows:

| Serial No. | Name of compound |
|---|---|
| A | 6-[(4-Methoxy-2-pyridyl)methylthio]-5H—[1,3]-dioxolo-[4,5-f]benzimidazole (GB 2 082 580) |
| B | 6-[(4-methoxy-2-pyridyl)methylsulfinyl]-5H—[1,3]-dioxolo[4,5-f]benzimidazole (GB 2 082 580) |
| C | 6,7-Dihydro-2-[(4-methoxy-2-pyridyl)methylthio]-1H—[1,4]-dioxino[2,3-f]benzimidazole (GB 2 082 580) |
| D | 6,7-Dihydro-2-[(4-methoxy-2-pyridyl)methylsulfinyl]-1H—[1,4]-dioxino[2,3-f]benzimidazole (GB 2 082 580) |
| 1 | 2,2-Difluoro-6-[(4-methoxy-2-pyridyl)methylsulfinyl]-5H—[1,3]-dioxolo[4,5-f]benzimidazole |
| 2 | 2,2-Difluoro-6-[(4-methoxy-3-methyl-2-pyridyl)methylsulfinyl]-5H—[1,3]-dioxolo[4,5-f]benzimidazole |
| 3 | 6,6,7-Trifluoro-6,7-dihydro-2-[(4-methoxy-2-pyridyl)methylsulfinyl]-1H—[1,4]-dioxino[2,3-f]benzimidazole |
| 4 | 6,6,7-Trifluoro-6,7-dihydro-2-[(4-methoxy-2-pyridyl)methylthio]-1H—[1,4]-dioxino[2,3-f]benzimidazole |
| 5 | 6,6,7-Trifluoro-6,7-dihydro-2-[(4-methoxy-3-methyl-2-pyridyl)methylsulfinyl]-1H-[1,4]-dioxino[2,3-f]benzimidazole |
| 6 | 6,6,7-Trifluoro-6,7-dihydro-2-[(4-methoxy-3-methyl-2- |

-continued

| Serial No. | Name of compound |
|---|---|
|  | pyridyl)methylthio]-1H—[1,4]-dioxino[2,3-f]benzimidazole |
| 7 | 2,2-Difluoro-6-[(4-methoxy-3-methyl-2-pyridyl)methylthio]-5H—[1,3]-dioxolo[4,5-f]benzimidazole |
| 8 | 2,2-Difluoro-6-[(4-methoxy-5-methyl-2-pyridyl)methylsulfinyl]-5H—[1,3]-dioxolo[4,5-f]benzimidazole |
| 9 | 6,6,7-Trifluoro-6,7-dihydro-2-[(4-methoxy-3,5-dimethyl-2-pyridyl)methylsulfinyl]-1H—[1,4]-dioxino[2,3-f]benzimidazole |
| 10 | 6-Chloro-6,7,7-trifluoro-6,7-dihydro-2-[(4-methoxy-3-methyl-2-pyridyl)methylsulfinyl]-1H—[1,4]-dioxino-[2,3-f]benzimidazole |

The influence of the compounds according to the invention on gastric lesion formation induced by pyloric ligature (4 h; so-called Shay rat) and oral administration of 100 mg/kg of acetylsalicylic acid, and the gastric secretion (HCl) in the course of 4 h in rats is shown in the following table.

| Protective effect on the stomach and inhibition of gastric secretion ||||| 
|---|---|---|---|---|
|  | Protective effect on the stomach (rats) | Gastric secretion (rats) |||
| Serial No. | n [Number of animals] | Inhibition of the lesion index, ED50* [mg/kg, perorally] | % inhibition of HCl secretion** | ED25* | ED50* [mg/kg, perorally] |
| A | 8 | >10.0 |  | >10.0 |  |
| B | 16 | ~5.0 |  |  |  |
| C | 23 | 30.0 | 19 | >30.0 | >30.0 |
| D | 40 | 30.0 | 0 | >30.0 | >30.0 |
| 1 | 64 | 0.6 | 25 | 0.6 | 0.9 |
| 2 | 56 | 0.4 | 30 | <0.3 | 0.6 |
| 3 | 56 | 0.45 | 23 | 0.5 | 1.4 |
| 4 | 40 | 0.6 | 25 | 1.0 | 1.7 |
| 5 | 80 | 0.35 | 35 | <0.3 | 0.6 |
| 6 | 24 | 0.6 | 20 | 0.7 | 1.4 |
| 7 | 24 | 0.6 | 25 | 0.6 | >1.0 |
| 8 | 23 | 0.5 | 17 | 1.0 | 2.5 |
| 9 | 32 | 0.5 | 15 | 0.7 | 1.0 |
| 10 | 16 | 0.4 | 25 | 0.4 | 0.7 |

*ED25 und ED50 = dose which reduces the lesion index or the HCl secretion (4h) in the rat stomach by 25 and, respectively, 50% in the treated group in comparison with the control group.
**after administration of the antiulcerous ED50.

The antiulcerogenic action was tested by the so-called Shay rat method:

Ulcers are caused in rats which have been fasted for 24 hours (female, 180–200 g, 4 animals per cage on a high grid) by pyloric ligature (under diethyl ether anesthesia) and oral administration of 100 mg/10 ml/kg of acetylsalicylic acid. The substances to be tested are administered orally (10 ml/kg) one hour before the pyloric ligature. The wound is closed by means of Michel clamps. 4 hours thereafter, the animals are sacrificed under ether anesthesia by Atlas dislocation and resection of the stomach. The stomach is opened longitudinally and attached to a cork plate, after the amount of gastric juice secreted (volume) and later its HCl content (titration with sodium hydroxide solution) have first been determined; the number and size (=diameter) of the ulcers present are determined under a stereomicroscope at 10-fold magnification. The product of the degree of severity (according to the following points scale) and number of ulcers serves as the individual lesion index.

Points scale:
no ulcers: 0
Ulcer diameter 0.1–1.4 mm: 1
1.5–2.4 mm: 2
2.5–3.4 mm: 3
3.5–4.4 mm: 4
4.5–5.4 mm: 5
>5.5 mm: 6

The reduction in the average lesion index of each treated group compared with the control group (=100%) serves as a measure of the antiulcerogenic effect. The ED25 and ED50 designate those doses which reduce the average lesion index or the HCl secretion by 25% or, respectively, 50% in comparison with the control.

TOXICITY

The LD50 of all the compounds tested is above 1,000 mg/kg [perorally] in mice.

What is claimed is:
1. A tricyclic ether of formula I

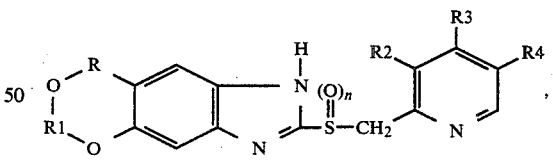

(I)

wherein
⁀R⁀ is a bond and
R1 is alkylene having 1 or 2 carbon atoms and being completly or partly substituted by fluorine, or chlorotrifluoroethylene, or
each of R and R1 is difluoromethylene,
R2 represents hydrogen or 1–3C-alkyl,
R3 represents hydrogen or 1–3C-alkyl or 1–3C-alkoxy,
R4 represents hydrogen or 1–3C-alkyl and
n represents the number 0 or 1, or
a salt thereof.

2. A compound according to claim 1, wherein ⁀R⁀ is a bond, R1 is alkylene having 1 or 2 carbon atoms and being completely or partly substituted by fluorine, R2 represents hydrogen or 1-3C-alkyl, R3 represents hydrogen or 1-3C-alkyl or 1-3C-alkoxy, R4 represents hydrogen or 1-3C-alkyl and n represents the number 0 or 1, or a salt thereof.

3. A compound according to claim 2, wherein R1 represents difluoromethylene or 1,1,2-trifluoroethylene, R2 represents a hydrogen atom or methyl, R3 represents a hydrogen atom or methoxy, R4 represents a hydrogen atom or methyl and n represents the number 0 or 1, and wherein R2, R3 and R4 are not simultaneously hydrogen atoms.

4. A compound according to claim 1 wherein R represents difluoromethylene, R1 represents difluoromethylene, R2 represents hydrogen or 1-3C-alkyl, R3 represents hydrogen or 1-3C-alkyl or 1-3C-alkoxy, R4 represents hydrogen or 1-3C-alkyl and n represents the number 0 or 1, or a salt thereof.

5. A compound according to claim 4, wherein R2 represents a hydrogen atom or methyl, R3 represents a hydrogen atom or methoxy, R4 represents a hydrogen atom or methyl and n represents the number 0 or 1, and wherein R2, R3 and R4 are not simultaneously hydrogen atoms.

6. A compound according to claim 1, wherein R is a bond, R1 is chlorotrifluoroethylene, R2 represents hydrogen or 1-3C-alkyl, R3 represents hydrogen or 1-3C-alkyl or 1-3C-alkoxy, R4 represents hydrogen or 1-3C-alkyl and n represents the number 0 or 1, or a salt thereof.

7. A compound according to claim 6, wherein R2 represents a hydrogen atom or methyl, R3 represents a hydrogen atom or methoxy, R4 represents a hydrogen atom or methyl and n represents the number 0 or 1, and wherein R2, R3 and R4 are not simultaneously hydrogen atoms.

8. A compound according to claim 1, wherein R is a bond, R1 represents difluoromethylene, 1,1,2-trifluoroethylene or 1-chloro-1,2,2-trifluoroethylene, R2 represents hydrogen or methyl, R3 represents methoxy, R4 represents hydrogen or methyl and n represents the number 0 or 1, or a pharmacologically-acceptable salt thereof.

9. A compound according to claim 2, wherein R1 represents difluoromethylene or 1,1,2-trifluoroethylene, R2 represents hydrogen or methyl, R3 represents methoxy, R4 represents hydrogen or methyl and n represents the number 0 or 1, or a pharmacologically-acceptable salt thereof.

10. A compound according to claim 6, wherein R1 represents 1-chloro-1,2,2-trifluoroethylene, R2 represents hydrogen or methyl, R3 represents methoxy, R4 represents hydrogen or methyl and n represents the number 0 or 1, or a pharmacologically acceptable salt thereof.

11. A compound according to claim 1 wherein n represents the number 0.

12. A compound according to claim 1 wherein n represents the number 1.

13. A compound according to claim 1, selected from the group consisting of 2,2-difluoro-6-[(4-methoxy-2-pyridyl)methylsulfinyl]-5H-[1,3]dioxolo[4,5-f]benzimidazole,
2,2-difluoro-6-[(4-methoxy-3-methyl-2-pyridyl)methylsulfinyl]-5H-[1,3]-dioxolo[4,5-f]benzimidazole,
6,6,7-trifluoro-6,7-dihydro-2-[(4-methoxy-2-pyridyl)methylsulfinyl]-1H-[1,4]-dioxino[2,3-f]benzimidazole,
6,6,7-trifluoro-6,7-dihydro-2-[(4-methoxy-2-pyridyl)methylthio]-1H-[1,4]-dioxino[2,3-f]benzimidazole,
6,6,7-trifluoro-6,7-dihydro-2-[(4-methoxy-3-methyl-2-pyridyl)methylsulfinyl]-1H-[1,4]-dioxino[2,3-f]benzimidazole,
6,6,7-trifluoro-6,7-dihydro-2-[(4-methoxy-3-methyl-2-pyridyl)methylthio]-1H-[1,4]-dioxino[2,3-f]benzimidazole,
2,2-difluoro-6-[(4-methoxy-3-methyl-2-pyridyl)methylthio]-5H-[1,3]dioxolo[4,5-f]benzimidazole,
2,2-difluoro-6-[(4-methoxy-5-methyl-2-pyridyl)methylsulfinyl]-5H-[1,3]-dioxolo[4,5-f]benzimidazole,
6,6,7-trifluoro-6,7-dihydro-2-[(4-methoxy-3,5-dimethyl-2-pyridyl)methylsulfinyl]-1H-[1,4]-dioxino[2,3-f]benzimidazole,
6-chloro-6,7,7-trifluoro-6,7-dihydro-2-[(4-methoxy-3-methyl-2-pyridyl)methylsulfinyl]-1H-[1,4]-dioxino[2,3-f]benzimidazole or a pharmacologically-acceptable salt thereof.

14. A compound according to claim 8 wherein R1 is difluoromethylene.

15. A compound according to claim 8 wherein R1 is 1,1,2-trifluoroethylene.

16. A compound according to claim 8 wherein R1 is 1-chloro-1,2,2-trifluoroethylene.

17. A method for treatment or prophylaxis of a disease of the stomach or intestine or one based on increased gastric acid secretion which comprises administering an effective amount of a pharmaceutically-acceptable compound according to claim 1 to a warm-blooded animal afflicted with or prone to attacks of such a disease.

18. A plural-component medicament composition comprising from 0.1 to 95 percent by weight of a pharmaceutically-acceptable compound according to claim 1.

19. A method for treatment or prophylaxis of a disease of the stomach or intestine or one based on increased gastric acid secretion which comprises administering an effective amount of a medicament composition according to claim 18 to a warm-blooded animal afflicted with or prone to attacks of such a disease.

20. A medicament composition useful for preventing and/or treating a gastrointestinal disease and comprising a pharmaceutical auxiliary and an effective amount of a pharmaceutically-acceptable compound according to claim 1.

21. The compound according to claim 1 which is 2,2-difluoro-6-[(4-methoxy-3-methyl-2-pyridyl)methylsulfinyl]-5H-[1,3]-dioxolo[4,5-f]benzimidazole or a pharmacologically-acceptable salt thereof.

22. A medicament composition useful for preventing and/or treating a gastrointestinal disease and comprising a pharmaceutical auxiliary and an effective amount of the compound of claim 21 or a pharmaceutically-acceptable salt thereof.

* * * * *